(12) United States Patent
Audeh

(10) Patent No.: US 6,689,267 B2
(45) Date of Patent: Feb. 10, 2004

(54) MULTI-PLATE ELECTROPHORESIS SYSTEM HAVING NON-MECHANICAL BUFFER CIRCULATION

(75) Inventor: Zuheir Audeh, Brookline, MA (US)

(73) Assignee: Center for Blood Research, Boston, MA (US)

( * ) Notice: Subject to any disclaimer, the term of this patent is extended or adjusted under 35 U.S.C. 154(b) by 0 days.

(21) Appl. No.: 10/094,757

(22) Filed: Mar. 11, 2002

(65) Prior Publication Data

US 2003/0168339 A1 Sep. 11, 2003

(51) Int. Cl.$^7$ .............................................. G01N 27/453
(52) U.S. Cl. ........................................................ 204/616
(58) Field of Search ................................ 204/456, 466, 204/606, 616, 621

(56) References Cited

U.S. PATENT DOCUMENTS

| 4,416,761 A | 11/1983 | Brown et al. |
| 4,702,814 A | * 10/1987 | Audeh ........................ 204/616 |
| 5,039,386 A | 8/1991 | Margolis |
| 5,047,135 A | 9/1991 | Nieman |
| 5,102,524 A | 4/1992 | Dutertre |
| 5,106,477 A | 4/1992 | Coleman |
| 5,514,255 A | 5/1996 | Gautsch |

FOREIGN PATENT DOCUMENTS

| EP | 134 622 A2 | 3/1985 |
| WO | 91/10901 | * 7/1991 |

* cited by examiner

*Primary Examiner*—Alex Noguerola
(74) *Attorney, Agent, or Firm*—Ropes & Gray, LLP; William G. Gosz

(57) ABSTRACT

An improved electrophoresis device includes first and second end reservoirs of buffer, and a separation tank between the end reservoirs. The separation tank fluidically interconnects the reservoirs and is configured to hold a stack of gel trays in an oriented electric field and covered by the buffer solution. At least one gas-driven fluid recirculation passage distinct from the separation tank drives buffer in one direction between the reservoirs, and stabilizes the buffer below the level of the trays, while stabilized buffer completes circulation between the stack of trays without thermal or chemical upset of the electrophoresis conditions over time. The device may have the same footprint as a conventional single-tray vessel, while having increased capacity for performing electrophoresis operations.

12 Claims, 3 Drawing Sheets

MULTI-PLATE ELECTROPHORESIS SYSTEM HAVING NON-MECHANICAL BUFFER CIRCULATION

TECHNICAL FIELD OF THE INVENTION

The present invention relates to systems for the electrophoretic separation of materials present in a sample wherein the materials have a range of molecular weights. The sample is applied to a gel or similar medium, e.g., on a tray in a vessel of buffer solution, and is subjected to an electric field for a time effective to separate components thereof. In particular the invention provides a stable multi-tray system for simultaneously processing multiple samples without the use of a mechanical buffer circulation pump.

BACKGROUND OF THE INVENTION

Electrophoresis is the migration of electrically charged particles in solution or suspension under the influence of an applied electric field. Each charged particle moves toward the electrode of opposite electrical polarity to its charge. For a given set of solution conditions, the velocity with which a particle moves divided by the magnitude of the electric field is a characteristic number called the electrophoretic mobility. The electrophoretic mobility is directly proportional to the magnitude of the charge on the particle, and is inversely proportional to the size of the particle. This property has been used to determine protein molecular weights; to distinguish among molecules by virtue of their individual net electrical charge; to detect amino acid changes from charged to uncharged residues or vice versa; and to separate different molecular weight species quantitatively as well as qualitatively. In particular, electrophoresis is widely used to separate, characterize and identify large molecules such as proteins and linear molecules such as DNA and RNA, and strands and fragments thereof. More complete and detailed information regarding the basic types of electrophoresis and the many applications for which each type of electrophoresis is utilized may be found in Freifelder, D., *Physical Biochemistry, Applications to Biochemistry and Molecular Biology*, 2nd edition, W. H. Freeman and Company, New York, 1982, pages 276–322.

The resolving power of electrophoresis can be greatly improved by the use of gel supporting media. Gel electrophoresis methods and electrophoretic apparatus which utilize gels such as starch, polyacrylamide, agarose, and agarose-acrylamide as supporting media are well established. The variety of different applications and the value of gel electrophoresis as a superior analytical and/or preparative tool is demonstrated by the many innovations in apparatus for electrophoresis. These are exemplified by U.S. Pat. Nos. 3,047,489; 4,234,400; 4,151,065; 3,980,546; 3,980,540; 3,932,265; and 3,553,097. Generally, agarose and polyacrylamide are the main types of gels used for electrophoretic analysis of nucleic acid. Typically, short to intermediate size fragments (below one thousand base pairs) are separated in polyacrylamide, while intermediate to high molecular weight fragments are separated in agarose gels. Often, the polyacrylamide gel is arranged in a vertical format or column, while the agarose gels are arranged on horizontal trays in slabs or beds. Typically, to obtain a good separation of DNA and other large molecular weight compositions (proteins and nucleic acids), electrophoresis must be performed on an extended time basis. One of the constant problems of electrophoretic analysis is the breakdown of the buffer used to control the pH of the gel medium due to the formation of acid ($H^+$) at the anode and the formation of base ($OH^-$) at the cathode over time. This problem is usually resolved by using a mechanical pump for circulating the buffer fluid between the anode containing buffer chamber and the cathode containing buffer chamber.

One electrophoresis device using a buffer circulation system is Applicant's previously patented gel electrophoresis apparatus shown in U.S. Pat. No. 4,702,814. That device has no mechanical circulation structure. It makes use of a pair of platinum electrodes, that are mounted in two buffer reservoirs provided at opposed ends of the device, and a tray supporting a gel bed positioned in a channel of fluid extending between the ends so that an electric field is established along the length of the channel. A hood is positioned below the surface of the buffer solution and covers the length of one of the end electrodes to capture evolved gas bubbles, and a fluid transfer passage extends from the hood at one reservoir upward and laterally to the reservoir at the other end of the apparatus. Bubbles of gas evolved from the underlying electrode enter the passage and drive buffer fluid from one reservoir to the other, creating an equalizing fluid transfer that prevents breakdown of the pH in both buffer reservoirs. The rate of transfer increases with the amount of evolved gas, and operates to transport the higher pH buffer from the cathode end and mix it with the lower pH buffer at the anode end, thus maintaining the buffer pH essentially constant throughout the whole system. The gas-driven circulation also promotes uniformity of temperature, so that the field separation characteristics remain constant and the band spacing is not subject to non-linear distortions at the central portion of the gel tray.

Other patents and marketed systems employ electromechanical pumps to effect buffer circulation and maintain substantial uniformity throughout the gel tray or trays. However, these systems are costly; the cost of a pump alone may be many hundreds of dollars. This is largely because the pump components must comply with fairly stringent standards of construction: the pump must be explosion-proof, electrically isolated, and emission-free for use in biological or laboratory situations.

While these devices have proven to be effective, recombinant DNA technologies, and the availability of polymerase chain reaction technology to amplify and produce effective sample sizes of arbitrary isolates, have expanded greatly the number of electrophoretic analyses performed, and have broadened the scope of such analyses to encompass broad applications in laboratory, industrial and clinical settings. As a result, greater throughput is needed in electrophoretic devices so that greater numbers of analyses can be run without requiring larger capital investments or taking up further space on testing benches.

Various techniques have been employed to refine the resolution or speed of the electrophoretic process for certain specific classes of molecules or conditions. For example, pulse field electrophoresis may be applied to better resolve very large DNA fragments, and extended gel lengths may be used to achieve finer resolution. Other techniques may involve the use of relatively low viscosity gels immobilized in capillary tubes for effecting the separation; the use of high field gradient, short path configurations; or the use of gradient gel concentration arrangements. In addition to having different column, capillary or bed formats, each gel material may present different effective porosity and characteristic ion mobilities. By way of example, the concentration of agarose used in the gel for DNA separations may vary from about 2% for separation of nucleic acid fragment under several thousand nucleotides in length, down to about 0.3% for separation of larger fragments having a size in the range of five thousand to sixty-thousand nucleotides. Similarly for polyacrylamide gels, the concentrations may range between about 3% for one-hundred to two-thousand nucleotide chains, up to about 20% for separating smaller molecules of lengths between about five and about one hundred nucleotides.

In electrophoretic separations, run lengths in vertical or horizontal format may range from about ten to about one-hundred centimeters, depending on the fragment size and the required degree of resolution. The voltage gradients may generally be about one to five volts per centimeter. Typically, a separation may take from one to about twenty hours depending upon resolution requirements and other parameters.

Various other techniques have been proposed to enhance speed or efficiency, or to more effectively integrate the separation process into a desired assay such as a DNA analysis. One such construction applies high electric fields, on the order of about five to about one-hundred volts per millimeter along the length of the gel axis in a relatively thin, e.g., (0.1 to 1.5 millimeter thick) gel bed, so as to effect fast separation over a length of under about two centimeters. Other thin bed techniques are used with greater length slabs, e.g., as in the Southern blot technique, in conjunction with other layers effective to transfer the bands of material, once separated, onto a blotter with high yield from the gel medium.

However, while the mechanism of gel electrophoresis allows a great many specialized variations, some of which can increase the speed of analysis in certain circumstances, the preponderance of separations in a working laboratory require a high-throughput separation apparatus that is both robust and inexpensive.

SUMMARY OF THE INVENTION

The present invention provides a device and method for carrying out electrophoretic separation of sample mixtures in a plurality of gels at the same time. The device of the invention provides increased throughput for separation analyses while taking up minimal space on a laboratory testing bench and requiring minimal capital investment as the device of the invention has a footprint no larger than existing single tray electrophoresis devices and requires no mechanical circulation pump.

The device of the invention includes a vessel containing buffer solution and having first and second end reservoirs and an intermediate channel fluidically interconnecting the two end reservoirs and configured to hold a stack of gel trays covereded by the buffer solution. A pair of electrodes, e.g., platinum wire electrodes, are mounted in the respective reservoirs at opposed ends of the vessel so that an oriented electric field is established along the length of the channel and in the trays between the reservoirs. Further, a gas driven recirculation assembly pumps the buffer from one end reservoir into buffer at the other end reservoir at a level below the level of the trays.

Preferably, the recirculation assembly is implemented with a hood that is positioned below the surface of the buffer solution and covering at least one of the electrodes to capture evolved gas bubbles, and a transfer passage that extends from a position near the top of the hood to the other end reservoir. Bubbles of gas evolved from the underlying electrode enter the passage and drive buffer fluid along the transfer passage from one end to the opposite end of the device, creating an equalizing fluid transfer that effectively neutralizes the fluid passing through the channel and over the gel trays. This prevents excessive buildup of acid or base in both buffer reservoirs and prevents breakdown of the buffer solution or the sample material. The rate of recirculation increases with the amount of evolved gas, and operates to transport the higher pH buffer from the cathode end and mix it with the lower pH buffer at the anode end, thus maintaining the buffer pH essentially constant. The gas-driven circulation is arranged with a return flow over the stacked gels, uniformizing temperature, so that electrophoretic field separation characteristics remain constant and the separation band spacing is not subject to non-linear distortions at the central portion of the gel tray due to temperature and/or pH gradients.

In a preferred embodiment, the gel trays are stackable, modular trays that each have one or more male registration elements on one or more sides, together with corresponding female registration elements, positioned in registry so that trays stack in alignment on one another without slipping or shifting. The stacked trays increase capacity of the device over the prior art without increasing footprint of the separation device, effectively multiplying separation throughput with minimal capital cost. The registration elements may be shaped such that the stacked trays have continuous confining sidewalls that effectively channel flow of buffer across the surface of each tray. The trays can also be dimensioned such that wall height provides a buffer spacing between layers that is comparable or somewhat less than the gel thickness. For example, a tray may have side walls about 1.5–2.0 centimeters high to support a gel layer one-half to about one centimeter thick leaving a 0.5 centimeter buffer space or recirculation return passage below the next higher tray. The trays may be formed of a suitable polymer, which may for example have a thickness of about 0.5 to 1.0 centimeters, so that at least one third and up to as much as one half of the volume of channel is occupied by gel layers and at least about one half of the volume of channel is occupied by the gel layers and gel supporting portions of the trays so that multiple trays may be stacked with sufficient recirculation flow to maintain generally uniform temperatures in the gel layers with only a nominal increase in buffer volume.

BRIEF DESCRIPTION OF THE DRAWINGS

These and other features of the invention and its various embodiments will be understood from the description herein of illustrative embodiments and comparative examples, taken together with the claims appended hereto and illustrative figures, wherein:

DETAILED DESCRIPTION OF THE INVENTION

Figure 1:
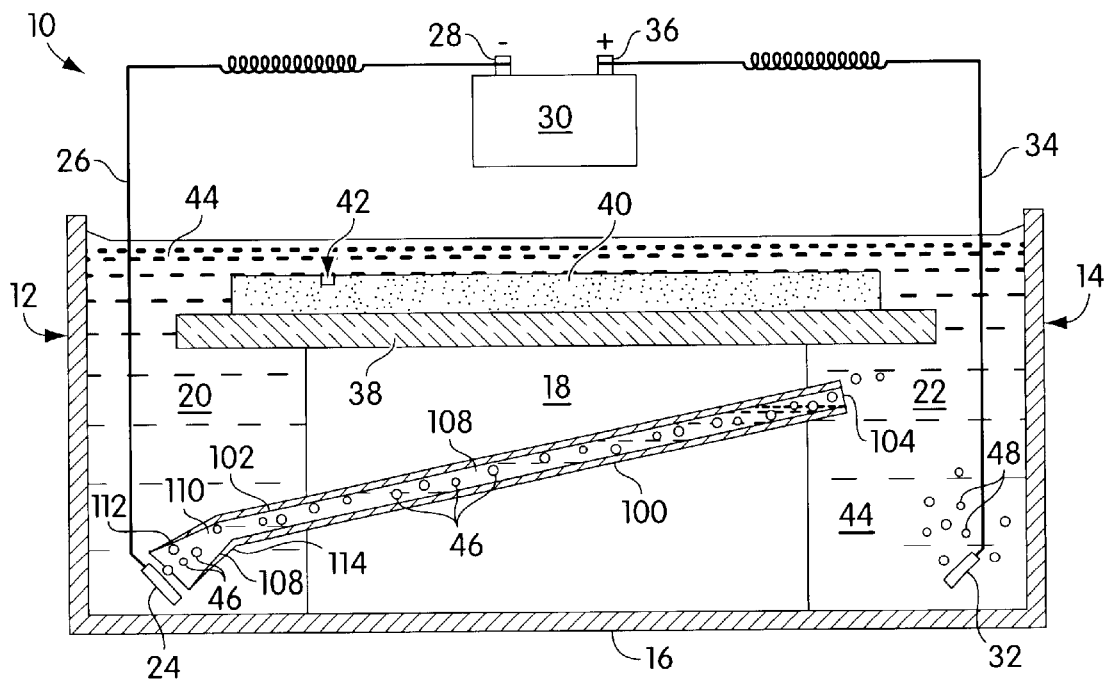
FIG. 1 illustrates a prior art electrophoresis device and vessel.

The device of the invention is a small footprint, low cost, high throughput electrophoresis device that can process electrophoretic separations in a plurality of gels simultaneously without the need for a mechanical circulation pump. FIG. 1 shows a prior art single tray electrophoresis apparatus 10 having a gas driven buffer recirculation system of the type generally set forth in applicant's earlier U.S. Pat. No. 4,702,814. As a number of the principles used in this device are employed in an electrophoresis device of the invention described below by reference to FIGS. 2 et seq., prior art electrophoresis apparatus 10 is first described in relative detail by reference to FIG. 1.

Electrophoresis apparatus 10 is illustrated in FIG. 1 in one mode of performing horizontal gel electrophoresis using a "submarine gel" in which the gel remains submerged within the buffer fluid throughout the entire duration of the electrophoresis. This embodiment is typically employed for the separation of DNA and RNA by molecular weight using agarose gels, however, a person of ordinary skill in the art will recognize that the principles of the invention described herein can be employed in electrophoretic apparatus in general regardless of specific application and/or regardless of whether a gel such as agarose, polyacrylmide, agarose-acrylamide or starch is used as the supporting media; in addition, it is expected and understood that the principles of the invention may be applied to electrophoretic apparatus known for other types of electrophoresis such as paper electrophoresis and cellulose acetate strip electrophoresis without limitation.

As illustrated by FIG. 1, an electrophoretic apparatus 10 is provided comprising a housing 12 having a plurality of side walls 14 and a base 16. The interior of the housing 12 contains a support block 18, typically composed of plastic or other inert material. Adjacent to the block 18 on both sides are a plurality of buffer chambers 20 and 22. Within the chamber 20 lies a cathode electrode 24 which is in electrical communication via a lead 26 to the negatively charged terminal 28 of a source of direct electrical current 30. Similarly, within the chamber 22 lies an anode electrode 32 which is in electrical communication via a lead 34 to the positive terminal 36 of the direct electrical current power source 30. Disposed upon the top planar surface of the support block 18 is a support plate 38 typically formed of plexyglass. The outer surface of the plate 38 supports a prepared gel medium 40, typically composed of agarose for DNA separations but which may be composed of other compositions or formulations as conventionally used for specific applications. A slot 42 has been made in the gel medium 40 as the site for depositing the sample intended to undergo electrophoresis. The interior void space of the housing 12 is filled with a preselected liquid buffer 44 prepared at known pH and having a predetermined buffering capacity. The choice of liquid buffer 44 for a specific pH value and buffering capacity is conventional and merely a matter of personal choice or convenience with regard to the particular application. With the introduction of electrical current, the cathode and anode electrodes become negatively and positively charged respectively. The sample deposited within the slot 42 will be drawn to the positively charged electrode and will migrate through the gel medium 40 in accordance with the individual net electrical charge and molecular weight of its components.

During normal operation, the buffer 44 will break down and the pH of the fluid in the chambers 20, 22 will be altered by the formation of acid at the anode 32 and by the formation of base at the cathode 24. Typically, an increase in electric current will result in a greater rate of gas formation at electrodes 24, 32. The presence of oxygen gas in the chamber 22 and of hydrogen gas in the chamber 20 is visibly identifiable by the gas bubbles 46 and 48 respectively which surround each of the electrodes 24, 32.

Electrophoresis apparatus 10 also includes a gas collection system, typically a gas trap which captures the gas bubbles generated at an electrode, and a conduit which extends at a positive incline or oblique angle from the interior of the cathode electrode containing chamber into the interior of the anode electrode containing chamber. As illustrated in FIG. 1, a conduit 100 is disposed through the entirety of the support block 18 with the conduits ends 102, 104 extending into the cathode containing chamber 20 and the anode containing chamber 22 respectively. The conduit end 102 expands into a gas trap 108 which overlays and partially envelops the cathode 24. The gas trap 108 is configured substantially as a scoop or hollow wedge and comprises a top surface 110 and two side walls 112, 114.

In use, the electric current will charge the cathode 24 and cause the formation of hydrogen gas bubbles 46 at cathode 24 which are captured and collected by the gas trap 108. Once within the gas trap 108, the gas bubbles are directed into the interior 106 of the conduit 100. The conduit 100 is a tube formed of plastic or other inert material. The gas bubbles 46 collected by the trap 108 migrate up the positive angle of incline of the conduit interior 106 until released via the conduit end 104 into the chamber 22. The migration of the gas bubbles 46 through the conduit interior 106 concomitantly carriers and propels basic buffer fluid from the chamber 20 through the conduit as an inherent part of the migration process. In this manner, the transfer of liquid from the chamber 20 into the chamber 22 is achieved directly in accordance with the rate of gas bubble migration through the conduit 100. The gas bubbles 46 and basic buffer liquid, having migrated through the entirety of the conduit 100, are released into the acidic (H+ containing) liquid in the anode containing chamber 22 to maintain the desired uniform pH value. As gas bubbles are generated at both the cathode 24 and at the anode 32, gas collection means and conduits can be employed at each electrode concurrently so that buffer flow and transfer will originate from both electrodes simultaneously.

An example illustrates the usefulness of this device in establishing a gas driven recirculation flow sufficient to provide pH equalization between chambers 20, 22 for a single electrophoresis run. The gas bubble migration and concomitant buffer transfer is empirically demonstrated by using the apparatus illustrated in FIG. 1 under actual test conditions. TAE Buffer (0.04 M Tris-acetate; 0.001 M EDTA) was prepared to provide a pH value of 8.0. This buffering liquid was added to the chambers 20 and 22 prior to connecting the respective electrodes to the D.C. power source. Upon application of a direct electrical current of 75 volts and 60 milliamperes, the rate of liquid flow from the negatively charged, cathode electrode containing chamber into the positively charged, anode electrode containing chamber was found to be 10+/−2 milliliters per minute. After allowing the electrophoresis apparatus to operate overnight (approximately 18 hours duration) at the described voltage, the pH value in both electrode chambers was found to be identical at pH 8.0.

Because the apparatus of FIG. 1 is a single tray apparatus, it can operate effectively with a relatively low electric current and appropriate pH throughout the buffer liquid and temperature throughout the gel may be maintained with a relatively small amount of buffer circulation, as might be provided with a one quarter inch diameter conduit 100. However, because the apparatus of FIG. 1 has only a single tray, the throughput of electrophoresis analyses for this apparatus is limited.

Figure 2:
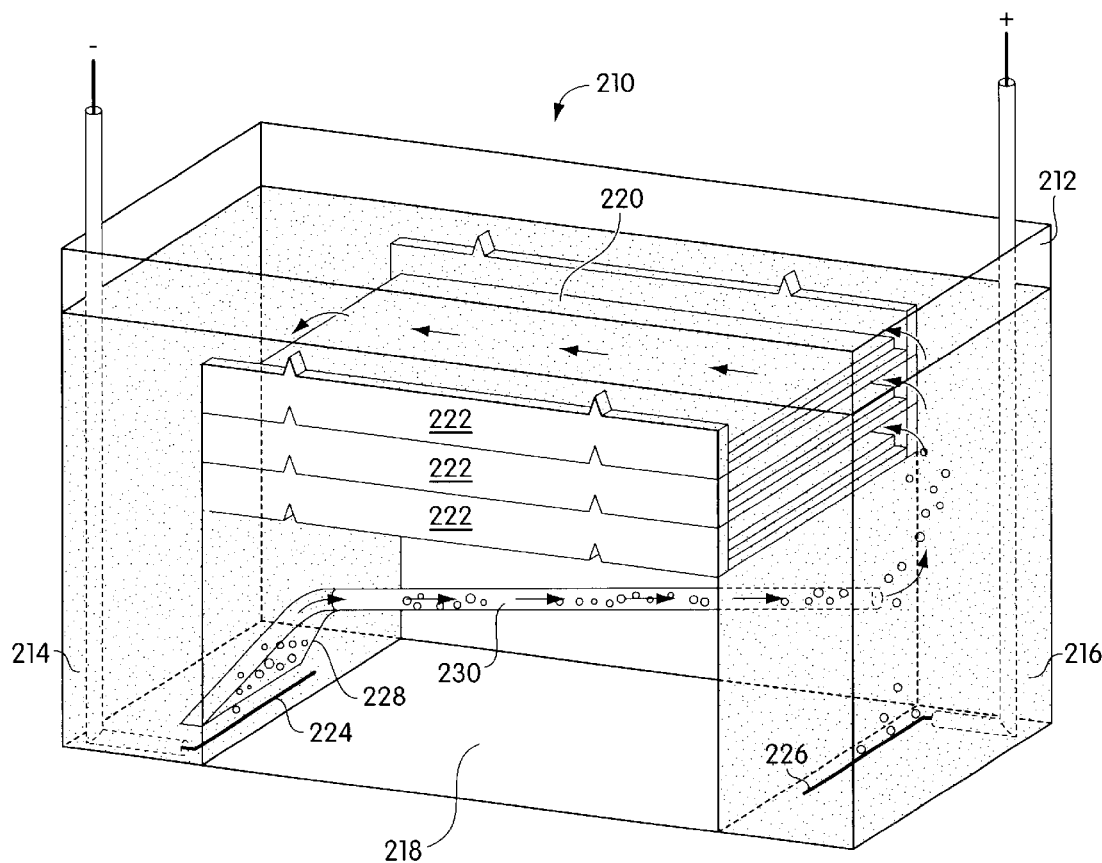
FIG. 2 illustrates a first embodiment of an electrophoresis device and vessel of the present invention.

Referring now to FIG. 2, a multi-tray electrophoresis device 210 of the invention is illustrated. The present invention provides a device and method for carrying out electrophoretic separation in a gel, of a sample mixture having material with a range of molecular weights. Electrophoresis device 210 includes a vessel 212 having first and second end reservoirs 214, 216 for holding a buffer solution. First and second end reservoirs 214, 216 are separated by a support block 218. When reservoirs 214, 216 are filled with buffer solution to a level that is higher than the height of support block 218, a channel 220 fluidically interconnects the two end reservoirs. Support block 218 is further configured to hold a stack of gel trays 222 that are covered by buffer solution in channel 220.

A pair of electrodes, i.e. cathode 224 and anode 226, are mounted one each in the first and second end reservoirs 214, 216, respectively, at opposed ends of vessel 212 so that an oriented electric field is established along the length of channel 220 between the reservoirs. In the illustrated embodiment, electrodes 224, 226 are configured as wires (such as, for example, platinum wires) that substantially span the width of each reservoir 214, 216 in a direction transverse to the direction of the oriented electric field established by the electrodes. Again as illustrated, electrode wires 224, 226 are substantially straight and are located within respective reservoirs 214, 216 proximate to, and equidistant from, support block 218.

Further, electrophoresis device 210 includes a gas driven recirculation assembly that mixes buffer from the first end reservoir 214 into buffer at the second end reservoir 216 at a level below the level of trays 222. As with apparatus 10 of FIG. 1, the recirculation assembly includes a gas trap 228 configured to trap gas bubbles forming from one of electrodes 224, 226 and a conduit 230 that extend from gas trap 228 through support block 218 at an inclined angle to the opposite reservoir. The rate of recirculation increases with the amount of evolved gas, and operates to transport the buffer from the buffer chamber at one end of the reservoir and mix it with the buffer in the chamber at the other end of the reservoir, thus maintaining the buffer pH essentially constant. The gas-driven circulation is arranged with a return flow over stacked gel trays 222 in channel 220 which tends to make the temperature of the gels uniform so that electrophoretic field separation characteristics remain constant and the separation band spacing is not subject to non-linear distortions at the central portion of gel trays 222 where temperature would otherwise become higher.

Figure 3:
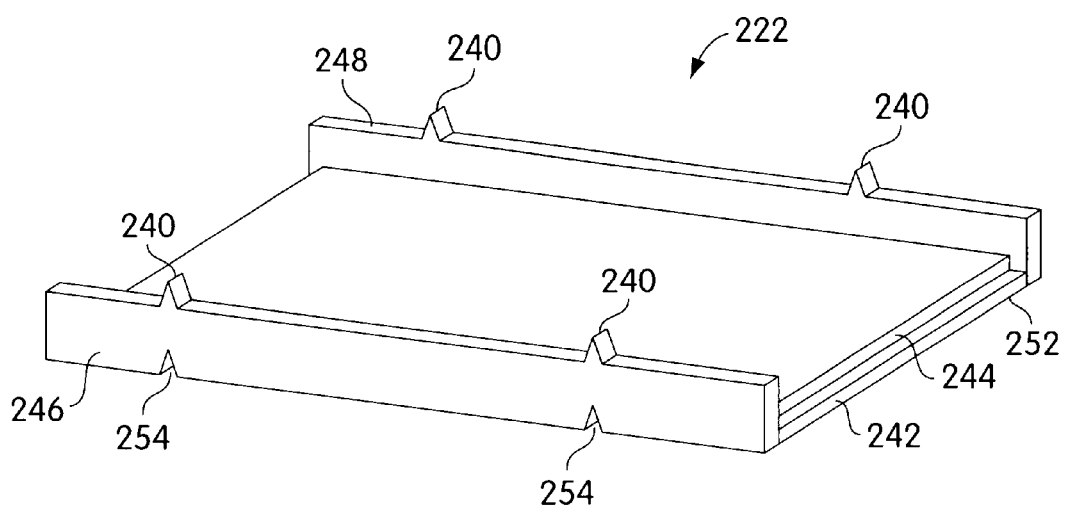
FIG. 3 illustrates a single tray used in the electrophoresis device of FIG. 2.

In a preferred embodiment, gel trays 222 (one gel tray is further illustrated in FIG. 3) are stackable, modular trays that each have a support plate 242 which supports a gel slab 244. Each tray 222 is open on first and second ends 250, 252 which correspond generally to the locations of the first and second end reservoirs 214, 216 and also has front 246 and rear 248 panels connected to support plate 242 which provide vertical registration of the support plates within channel 220. That is, front and rear panels 246, 248 are sized so as to maintain a desired spacing between the support plates 242 and/or gel slabs 244 of adjacent plates so that buffer fluid will flow between a given gel slab 244 and the support plate 242 above it. In this way, recirculation of buffer fluid also causes buffer fluid to flow over each gel slab 244, causing the temperature within each slab to be generally uniform.

The voltage applied between electrodes 224, 226 in electrophoresis device 210 is typically up to or on the order of 100 volts, similar to the voltage used in single tray apparatus 10. In multi-tray device 210, however, the current is proportional to the number of gels used, and while the current applied for a single gel will generally vary up to about 0.1 amperes, device 210 may be called upon to operate with as much as 1.0 ampere. Higher currents will tend to cause the pH in both buffer reservoirs to breakdown more quickly and make the gel slabs 244 heat more quickly, however, the rate of gas generation at the electrodes will also be proportional to the current applied, meaning that at larger currents, where more recirculation is desired both to prevent buffer breakdown and to make gel 244 temperature uniform, more gas bubbles are available to drive buffer recirculation. Accordingly, conduit 230 is preferably larger in cross-section than conduit 100 of single tray electrophoresis apparatus 10 and, when used to electrophorese three to four gels 244 simultaneously, preferably has a diameter of at least about one half inch. While one gas collecting trap is illustrated in FIG. 2, more than one gas collecting trap and conduit in combination can be used within a single electrophoresis device 210 for the purpose of fluid transfer. Since gas bubbles are generated at cathode 224 and at the anode 226, gas collection means and conduits can be employed at each electrode concurrently so that buffer flow and transfer will originate from both electrodes simultaneously. If a gas collecting trap is provided at only one electrode, it is preferable to provide it at cathode 224 as the cathode generates twice as much (by volume) hydrogen gas as the anode generates oxygen gas.

Trays 222 are preferably dimensioned such that front/rear panel 246, 248 height provides a buffer spacing between layers that is comparable or somewhat less than the thickness of gel slab 244. For example, front/rear panels 246, 248 may have a height of about 1.5–2.0 centimeters to support a gel layer 244 having a height of about one-half to about one centimeter thick, leaving a 0.5 centimeter buffer space or recirculation return passage below the next higher tray. Trays 222 may be formed of a suitable polymer, which may for example have a thickness of about 0.5 to 1.0 centimeters. Thus, in this preferred example, at least one third and up to as much as one half of the volume of channel 220 is occupied by gel slabs 244 at least about one half of the volume of channel 220 is occupied by the gel slabs and support plates 242 so that multiple trays 222 may be stacked with sufficient recirculation flow to maintain generally uniform temperatures in the gel slabs with only a nominal increase in buffer volume.

One or more male registration features 240 can also be formed on at least one side of one or more of the front and rear panels 246, 248 with corresponding female registration features 254 on an opposed side of the front and rear panels so that as trays 222 are stacked, they will be appropriately registered in a first-second end 250, 252 direction and will stay in alignment with each other without slipping or shifting. Support block 218 may also include registration features, in the illustrated embodiment male registration features 240, so that the stack of trays 222 is aligned with respect to vessel 212. Trays 222 so stacked increase capacity of the device over the prior art without increasing footprint of the separation device, effectively multiplying separation throughput with minimal capital cost.

What is claimed is:

1. An electrophoresis device comprising:
   a vessel having a first end reservoir, a second end reservoir, and an intermediate channel for fluidically interconnecting the first and the second end reservoirs at respective upper regions thereof, the vessel being configured to hold an amount of ionic buffer solution;
   a plurality of trays, each tray supporting a gel for separating a sample by electrophoresis, the trays and the intermediate channel being configured such that the trays are stacked in the intermediate channel to be covered by the ionic buffer solution;
   a respective electrode mounted in each end reservoir such that a voltage applied across the respective electrodes is effective to establish an electric field oriented along an axis between the reservoirs when the vessel is filled with an ionic buffer solution; and a non-mechanical buffer recirculation assembly powered by gas generated by at least one of the electrodes and operative to mix ionic buffer solution from one end reservoir into ionic buffer solution at the other end reservoir to prevent buffer breakdown, said recirculation assembly comprising a fluid transfer passage extending between the two end reservoirs and positioned in a support block beneath the intermediate channel, said recirculation assembly operating at a level below the level of the plurality of trays such that ionic buffer solution circulates continuously between the trays to maintain uniform electrophoresis conditions in gels supported by the trays.

2. The electrophoresis device of claim 1, wherein the non-mechanical buffer recirculation assembly comprises a gas catcher positioned over at least one electrode, and wherein the fluid transfer passage is positioned with a first end at the gas catcher such that gas evolved at said one electrode drives buffer fluid along the transfer passage to the other end reservoir.

3. The electrophoresis device of claim 2, wherein the gas catcher includes a hood that is positioned below the surface of buffer over said one electrode to capture evolved gas bubbles, and the fluid transfer passage extends from a position toward the top of the hood such that bubbles of gas evolved from said one electrode enter the passage and drive buffer fluid from one end to the opposite end of the device to prevent pH breakdown of buffer.

4. The electrophoresis device of claim 1, wherein the male and female registration elements are shaped such that the stacked trays have continuous confining sidewalls effective to channel flow of buffer across the surface of each tray.

5. The electrophoresis device of claim 1, wherein the channel includes a registration element configured so that the trays may be stacked in registry with the channel without slipping.

6. The electrophoresis device of claim 1, wherein each of the plurality of trays hold a gel layer and are dimensioned to provide a free buffer spacing between trays that is less than or equal to a thickness of the gel layer.

7. The electrophoresis device of claim 1, wherein each of the plurality of trays holds a gel layer.

8. The electrophoresis device of claim 7, wherein each of the plurality of trays includes a support plate that supports the gel layer, and each of the gel layers is dimensioned so that at least about one third of the volume of the channel is taken up by gel layers.

9. The electrophoresis device of claim 7, wherein each of the plurality of support plates and gel layers is dimensioned so that at least about one half of the volume of the intermediate channel is taken up by the support plates and the gel layers.

10. The electrophoresis device of claim 7, wherein each of the plurality of support plates and gel layers are dimensioned so that the gel layers have a thickness between about 0.5 and 1.0 centimeters and the support plates have a thickness between about 0.5 and 1.0 centimeters.

11. The electrophoresis device of claim 10, wherein an overall height of each tray is between about 1.5 and 2.0 centimeters.

12. The electrophoresis device of claim 7, wherein each of the plurality of trays is dimensioned and spaced to support a gel layer covered by about 0.5 centimeter buffer below the next higher tray.

* * * * *